US009649254B2

(12) United States Patent
Frishman

(10) Patent No.: US 9,649,254 B2
(45) Date of Patent: May 16, 2017

(54) MEDICAL VIAL CAP

(71) Applicant: WORLD BOTTLING CAP, LLC, Carrollton, TX (US)

(72) Inventor: Abe Frishman, Carrollton, TX (US)

(73) Assignee: WORLD BOTTLING CAP, LLC, Carrollton, TX (US)

( * ) Notice: Subject to any disclaimer, the term of this patent is extended or adjusted under 35 U.S.C. 154(b) by 0 days.

(21) Appl. No.: 14/098,208

(22) Filed: Dec. 5, 2013

(65) Prior Publication Data

US 2015/0157535 A1 Jun. 11, 2015

Related U.S. Application Data

(63) Continuation-in-part of application No. 13/267,264, filed on Oct. 6, 2011, now Pat. No. 8,608,006, which (Continued)

(51) Int. Cl.

*A61B 19/00* (2006.01)
*A61J 1/14* (2006.01)

(Continued)

(52) U.S. Cl.

CPC ............ *A61J 1/1412* (2013.01); *B65D 41/42* (2013.01); *B65D 47/141* (2013.01); *B65D 47/36* (2013.01);

(Continued)

(58) Field of Classification Search

CPC .............................. A61J 1/1412; A61J 1/1406

(Continued)

(56) References Cited

U.S. PATENT DOCUMENTS

| | | | |
|---|---|---|---|
| 1,294,171 | A | 2/1919 | Rockwell |
| 1,516,207 | A | 11/1924 | Rockwell |

(Continued)

FOREIGN PATENT DOCUMENTS

| | | |
|---|---|---|
| CN | 2094345 | 1/1992 |
| DE | 2015629 | 10/1971 |

(Continued)

OTHER PUBLICATIONS

International Preliminary Report on Patentability pertaining to application ser. No. PCT/US14/14555, the international counterpart application to the present application.

(Continued)

*Primary Examiner* — Leslie Deak
(74) *Attorney, Agent, or Firm* — James H. Ortega; Carstens & Cahoon, LLP

(57) ABSTRACT

A crown, for a medical vial opening, has a top portion and a skirt surrounding the top portion. The skirt terminates at a lower edge defined in a first horizontal plane. An opener assembly is mounted to a portion of the top. A first scoring line extends from the portion of the top to which the opener assembly is mounted to the lower edge of the skirt in a continuous radial direction, and a second scoring line provides an upper radial segment extending from the opener assembly to the skirt along a radial axis, and a lower annular segment that extends circumferentially along the skirt in an annular direction and extending from a terminus of the upper radial segment. The lower annular segment is defined in a second horizontal plane equidistant to the first horizontal plane associated with the lower edge of the skirt.

10 Claims, 14 Drawing Sheets

Related U.S. Application Data is a continuation of application No. 11/698,247, filed on Jan. 25, 2007, now Pat. No. 8,061,544, which is a continuation-in-part of application No. PCT/US2006/002421, filed on Jan. 24, 2006.

(60) Provisional application No. 60/758,725, filed on Jan. 14, 2006.

(51) Int. Cl.

| | |
|---|---|
| ***B65D 41/42*** | (2006.01) |
| ***B65D 47/14*** | (2006.01) |
| ***B65D 47/36*** | (2006.01) |
| ***B65D 51/00*** | (2006.01) |
| ***B65D 51/18*** | (2006.01) |
| *B65D 17/00* | (2006.01) |

(52) U.S. Cl.
CPC ........... *B65D 51/002* (2013.01); *B65D 51/18* (2013.01); *B65D 17/163* (2013.01); *B65D 17/165* (2013.01); *B65D 2251/0025* (2013.01); *B65D 2251/0093* (2013.01)

(58) Field of Classification Search
USPC .......................................................... 604/415
See application file for complete search history.

(56) References Cited

U.S. PATENT DOCUMENTS

| | | | | |
|---|---|---|---|---|
| 2,046,173 | A | 6/1936 | Lenhoff | |
| 2,191,447 | A | 2/1940 | Beardsley | |
| 2,387,955 | A * | 10/1945 | Tilson .................. | B65D 51/002 215/230 |
| 3,199,705 | A | 8/1965 | Brockett | |
| 3,206,055 | A | 9/1965 | Helbling | |
| 3,268,368 | A | 8/1966 | Mackiw et al. | |
| 3,462,036 | A | 4/1969 | Chaolu | |
| 3,451,367 | A | 6/1969 | Hendrickson | |
| 3,480,173 | A | 11/1969 | Wheaton | |
| 3,522,899 | A | 8/1970 | Siemonsen et al. | |
| 3,545,638 | A | 12/1970 | Brown | |
| 3,556,336 | A | 1/1971 | Coop | |
| 3,598,272 | A | 8/1971 | Bustamante et al. | |
| 3,630,405 | A | 12/1971 | Podesta | |
| 3,724,700 | A | 4/1973 | Heffran | |
| 3,734,333 | A | 5/1973 | Foss | |
| 3,743,129 | A | 7/1973 | Willis et al. | |
| 3,823,841 | A | 7/1974 | Lovejoy | |
| 3,834,573 | A | 9/1974 | Amos | |
| 3,851,793 | A | 12/1974 | Brown | |
| 3,870,184 | A | 3/1975 | Fuchs et al. | |
| 3,905,503 | A | 9/1975 | Fraze | |
| 3,920,142 | A | 11/1975 | Vandrebeck et al. | |
| 3,940,254 | A | 2/1976 | McMullen et al. | |
| 3,958,710 | A | 5/1976 | Harding et al. | |
| RE28,862 | E | 6/1976 | Siemonsen et al. | |
| 3,963,140 | A | 6/1976 | Harding | |
| 3,963,141 | A | 6/1976 | Liu | |
| 4,004,705 | A | 1/1977 | Fujio | |
| 4,060,172 | A | 11/1977 | Amabili | |
| 4,087,018 | A | 5/1978 | Tebbutt | |
| 4,089,753 | A | 5/1978 | McMullen et al. | |
| 4,176,014 | A | 11/1979 | Ruscoe et al. | |
| 4,184,605 | A | 1/1980 | Hanson | |
| 4,247,374 | A | 1/1981 | Ruscoe et al. | |
| 4,279,968 | A | 7/1981 | Ruscoe et al. | |
| 4,318,493 | A | 3/1982 | Jacobsen et al. | |
| 4,453,644 | A | 6/1984 | Berglund | |
| RE31,869 | E | 4/1985 | Harding | |
| 4,534,481 | A | 8/1985 | Summers et al. | |
| 4,579,761 | A | 4/1986 | Ruscoe et al. | |
| 4,768,667 | A | 9/1988 | Magnusson | |
| 5,020,686 | A | 6/1991 | Dutt | |
| 5,069,345 | A | 12/1991 | Irwin | |
| 5,080,245 | A | 1/1992 | Conard | |
| 5,143,241 | A | 9/1992 | Szymanski | |
| 5,145,084 | A | 9/1992 | Murayama et al. | |
| 5,458,253 | A | 10/1995 | Shapcott | |
| 5,924,739 | A | 7/1999 | Garbutt | |
| 6,006,933 | A | 12/1999 | Henning et al. | |
| 6,138,856 | A | 10/2000 | Ghim et al. | |
| 6,283,318 | B1 | 9/2001 | Lee | |
| 8,061,544 | B2 | 11/2011 | Frishman | |
| 8,276,773 | B2 * | 10/2012 | Frishman ............... | B65D 41/12 215/255 |
| 8,365,940 | B2 | 2/2013 | Frishman | |
| 8,944,264 | B2 | 2/2015 | Frishman | |
| 2002/0104852 | A1 | 8/2002 | Staniszewski et al. | |
| 2003/0201266 | A1 | 10/2003 | Steffan | |
| 2005/0279432 | A1 | 12/2005 | Takeuchi et al. | |
| 2007/0181526 | A1 | 8/2007 | Frishman | |
| 2010/0096355 | A1 | 4/2010 | Chaolu | |
| 2010/0200534 | A1 | 8/2010 | Frishman | |
| 2012/0261380 | A1 | 10/2012 | Frishman | |

FOREIGN PATENT DOCUMENTS

| | | | |
|---|---|---|---|
| DE | 8527425 | | 1/1986 |
| DE | 3906112 | | 8/1990 |
| DE | 29600761 | | 1/1997 |
| EP | 0262767 | | 4/1988 |
| GB | 1279068 | | 6/1976 |
| GB | 1540229 | | 2/1979 |
| JP | 602448 | A | 1/1985 |
| WO | 0051906 | | 9/2000 |
| WO | 0071430 | | 11/2000 |
| WO | 2006048903 | | 5/2006 |

OTHER PUBLICATIONS

Supplemental European Search Report for EP14745376.5 dated Sep. 8, 2016.
International Search Report for PCT/US2006/002421 dated Oct. 17, 2006.
International Preliminary Report on Patentability for PCT/US2006/002421, dated Jul. 15, 2008.
International Search Report for PCT/US2014/014555, dated May 22, 2014.

* cited by examiner

MEDICAL VIAL CAP

CROSS-REFERENCE TO RELATED APPLICATIONS

This application is a continuation-in-part of U.S. application Ser. No. 13/267,264, filed Oct. 6, 2011, now U.S. Pat. No. 8,608,006, which is a continuation in part of U.S. application Ser. No. 11/698,247, filed Jan. 25, 2007, now U.S. Pat. No. 8,061,544, which is a continuation in part of International Application No. PCT/US2006/002421, filed Jan. 24, 2006, which claims the benefit of U.S. Provisional Application No. 60/758,725, filed Jan. 14, 2006, the disclosures of which applications are incorporated herein by reference.

FIELD OF THE DISCLOSURE

The present disclosure relates to caps and crowns for medical vials and other containers, and in particular, to a manual pull-to-open vial cap.

BACKGROUND

Fluid medicines are often stored in vials for dispensing with a syringe. A common type of vial is the open circle lens vial. This type of vial is familiar to anyone who has gotten a shot at the doctor's office, and typically has a thin metal top cover which protects a pierceable membrane that is sealed to the rim of the vial. Some modern vial covers have a plastic frame that rotates around the vial rim to align with a marking on the vial to indicate it is in proper opening position. The plastic frame then facilitates opening the metal cover that is attached to the frame. When the frame is pried up, the metal cover tears open across the top and down the side of the vial, the thin metal then breaks into two or more segments along the rim of the vial for easy removal of the frame and the metal cover to expose the membrane to be pierced by a syringe.

The problems with the standard open circle lens vials described above include the requirement to align markings on the plastic frame and the vial prior to opening and the creation of sharps by the metal segments of the cover.

Aligning markings can be difficult if the ambient lighting is poor or if the nurse has poor eyesight. Even when markings are aligned, the frame may not lifted up as expected if the tolerance for the markings is too strict so that one has to experiment through trial and error to make the alignment work. If the tolerances for the alignment are too loose, it defeats the purpose of aligning the markings in the first place.

Hospitals and doctors' offices are always conscious of sharps such as needles and have protocols and equipment to isolate and dispose of sharps. This is particularly a concern if patients are in the area where there are sharps. It is, therefore, in the interest of medical professionals to reduce the number of sharps in their practice.

There is a need, therefore, for a medical vial cap that is easy to open manually, does not require alignment yet is safe, and which reduces sharps. To provide these advantages, certain features of the bottle crown described in the patents and patent applications related to this application have been adapted here to medical vial caps, in particular the opener assembly and the score lines, which advantageously allow a medial vial cap to be opened in a manner comparable to the beverage bottle cap previously described.

SUMMARY

A crown, for a medical vial opening, has a top portion and a skirt surrounding the top portion. The skirt terminates at a lower edge defined in a first horizontal plane. An opener assembly is mounted to a portion of the top. A first scoring line extends from the portion of the top to which the opener assembly is mounted to the lower edge of the skirt in a continuous radial direction, and a second scoring line provides an upper radial segment extending from the opener assembly to the skirt along a radial axis, and a lower annular segment that extends circumferentially along the skirt in an annular direction and extending from a terminus of the upper radial segment, the lower annular segment defined in a second horizontal plane equidistant to the first horizontal plane associated with the lower edge of the skirt.

BRIEF DESCRIPTION OF THE DRAWINGS

The detailed description that follows, by way of non-limiting examples of embodiments, makes reference to the noted drawings in which reference numerals represent the same parts throughout the several views of the drawings, and in which.

DETAILED DESCRIPTION

In view of the foregoing, through one or more various aspects, embodiments and/or specific features or sub-components, the present disclosure is thus intended to bring out one or more of the advantages that will be evident from the description. The present disclosure makes reference to one or more specific embodiments by way of illustration and example. It is understood, therefore, that the terminology, examples, drawings and embodiments are illustrative and are not intended to limit the scope of the disclosure. The terms "crown" and "cap" may be used interchangeably in the description that follows.

Figure 1:
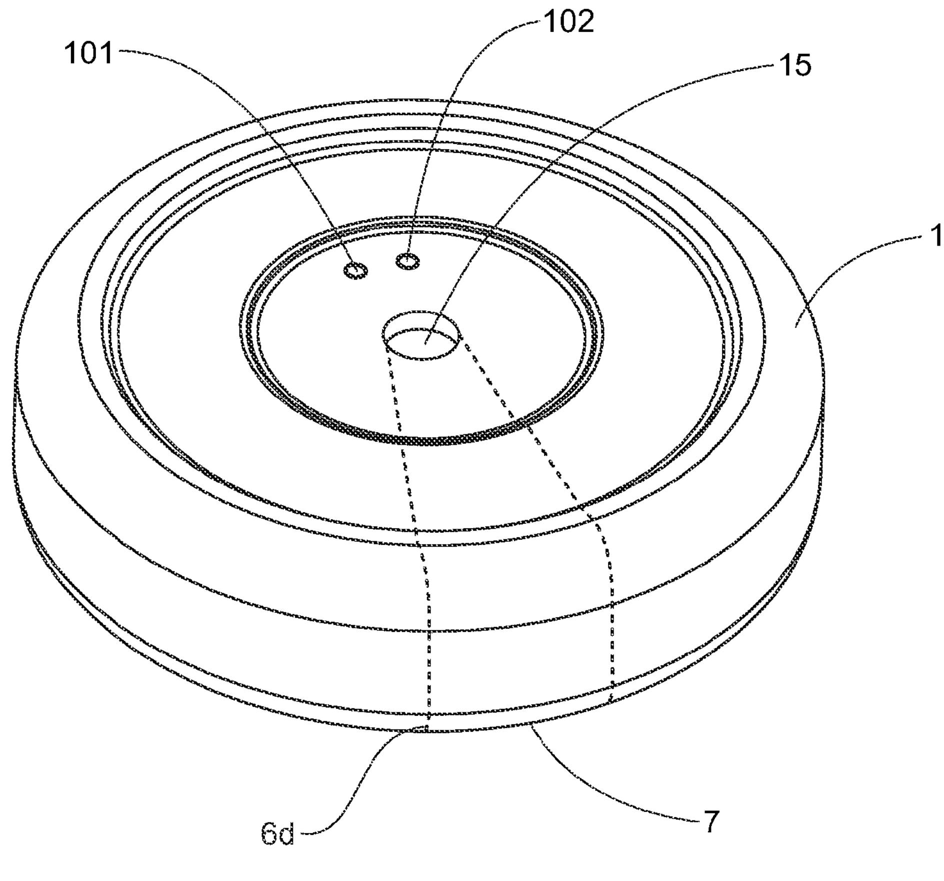
FIG. 1 is a isometric top view diagrammatic illustration of an exemplary embodiment of a medical vial cap of the present disclosure.

FIG. 1 is a isometric top view diagrammatic illustration of an exemplary embodiment of a medical vial cap of the present disclosure. Frangible score lines 6*d* extend in a straight line from opener assembly attachment position 15 to the edge 7 of the cap 1. Dimples 101, 102 are positioned on the top of cap 1 so as to secure an opener assembly in position by inhibiting rotation of the opener assembly around attachment position 15.

Figure 2:
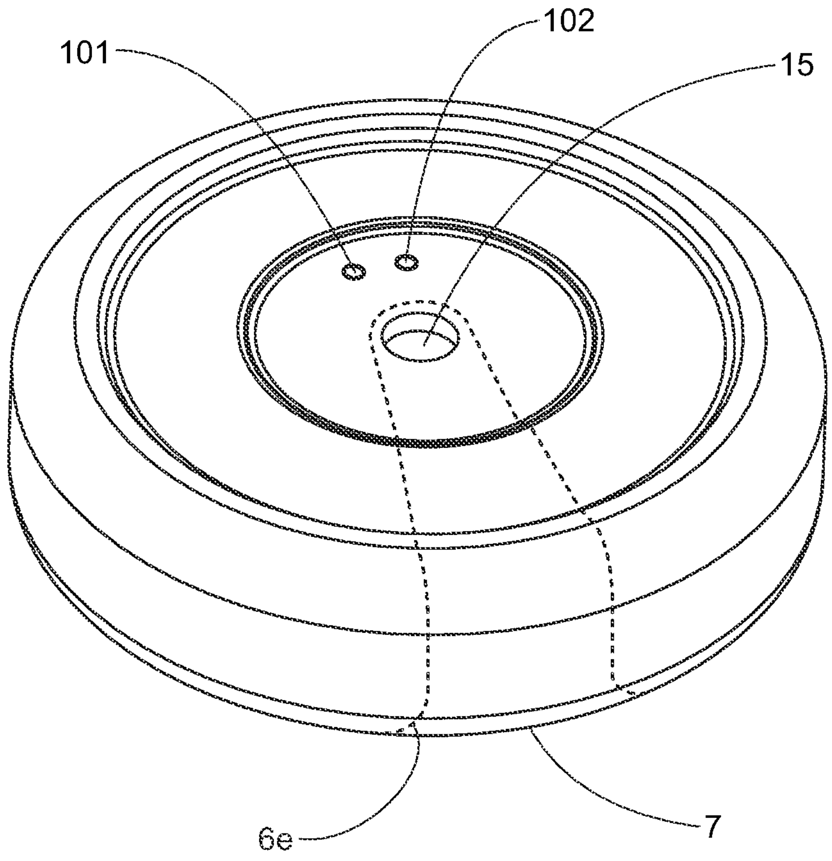
FIG. 2 is an isometric top view diagrammatic illustration of an alternative embodiment of the cap of FIG. 1.

FIG. 2 is an isometric top view diagrammatic illustration of an alternative embodiment of the cap of FIG. 1. Score line 6*e* traces a continuous path from edge 7 around opener assembly position 15, between position 15 and dimples 101,102, and back to a different position on edge 7. FIG. 2 depicts an alternative embodiment of score line 6*e* in which the score line curves to intersect edge 7.

Figure 3:
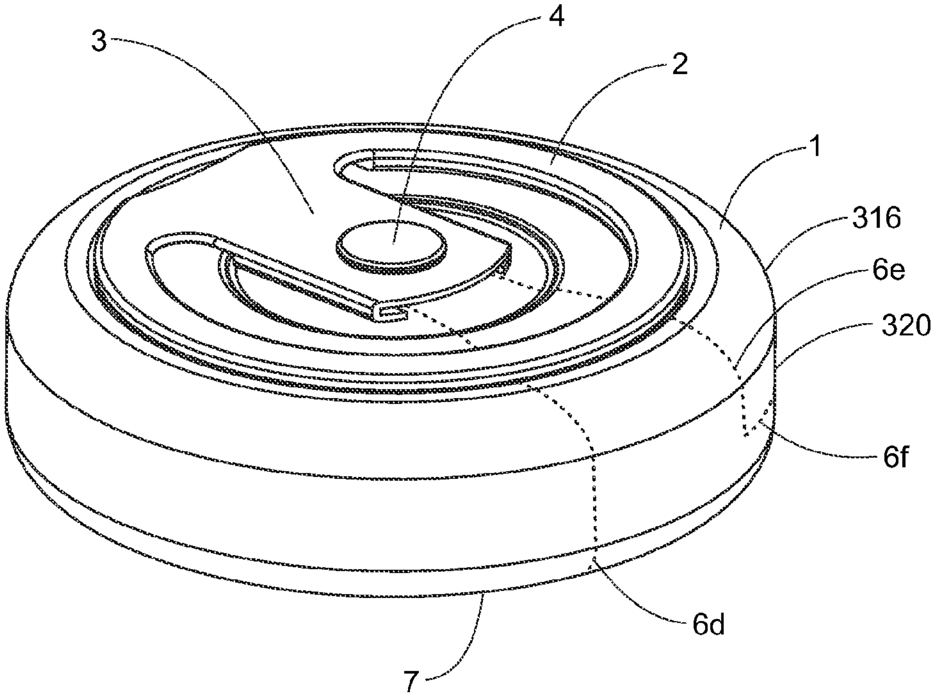
FIG. 3 is an isometric top view diagrammatic illustration of an alternative embodiment of the cap of FIG. 1 having an opener assembly.

FIG. 3 is an isometric top view diagrammatic illustration of an alternative embodiment of the cap of FIG. 1 having an opener assembly. The opener assembly has pull tab ring 2, pull tab 3 and an attachment means to attach the assembly to cap 1, such as a rivet. In yet another alternative embodiment of the score lines, score line 6*e* descends below the top 310 of cap 1 and curves to form score line 6*e*, which traverse along the side 320 substantially equidistant from top 310 and edge 7.

Figure 4:
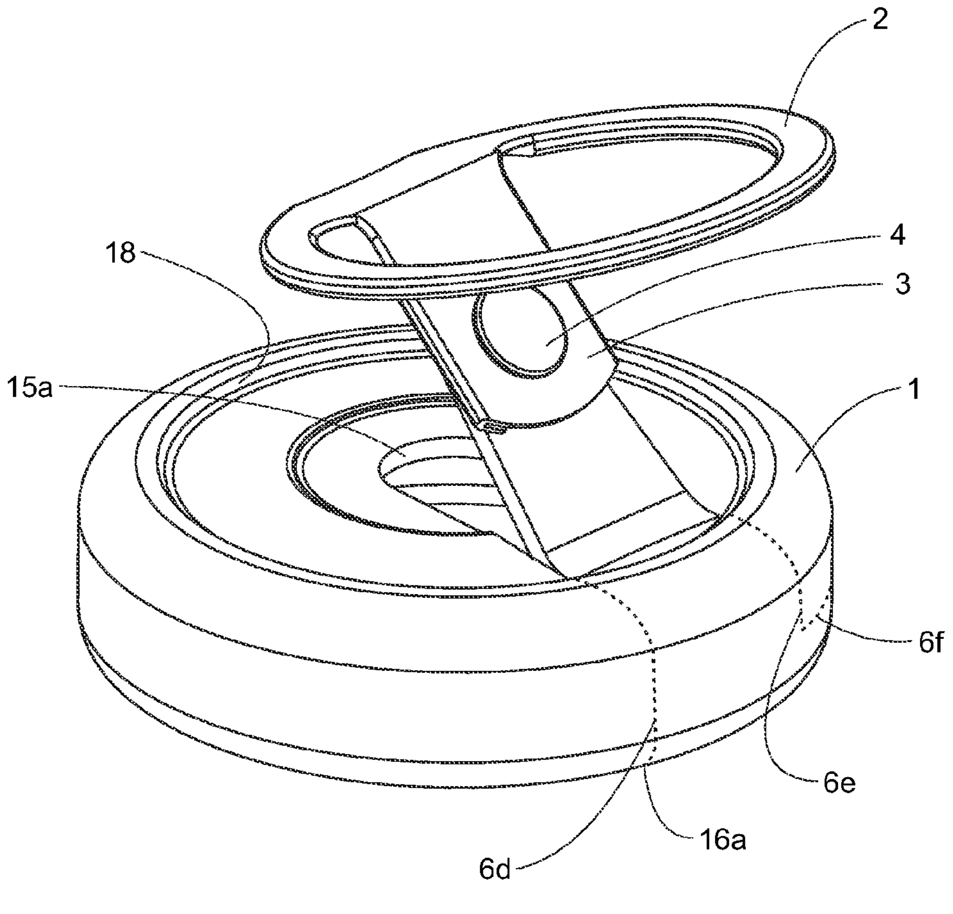
FIG. 4 is an isometric top view diagrammatic illustration of the alternative embodiment of the cap of FIG. 3, partially opened.

FIG. 4 is an isometric top view diagrammatic illustration of the alternative embodiment of the cap of FIG. 3, partially opened. Pull tab ring 2 is a least partially deformable so that it can be lifted for a finger to fit into the ring. Pulling pull tab ring 2 causes frangible cap 1 to tear open along score lines 6*d*, 6*e* and creating opening 15*a* beneath pull tab 3. Specific exemplary embodiments provide recessed depression 18 in crown 1 to house the opener assembly so that, in the unopened position, pull tab ring 2 is substantially flush with the top of cap 1. Score line 6*d* terminates in a straight line at terminus 16*a*.

Figure 5:
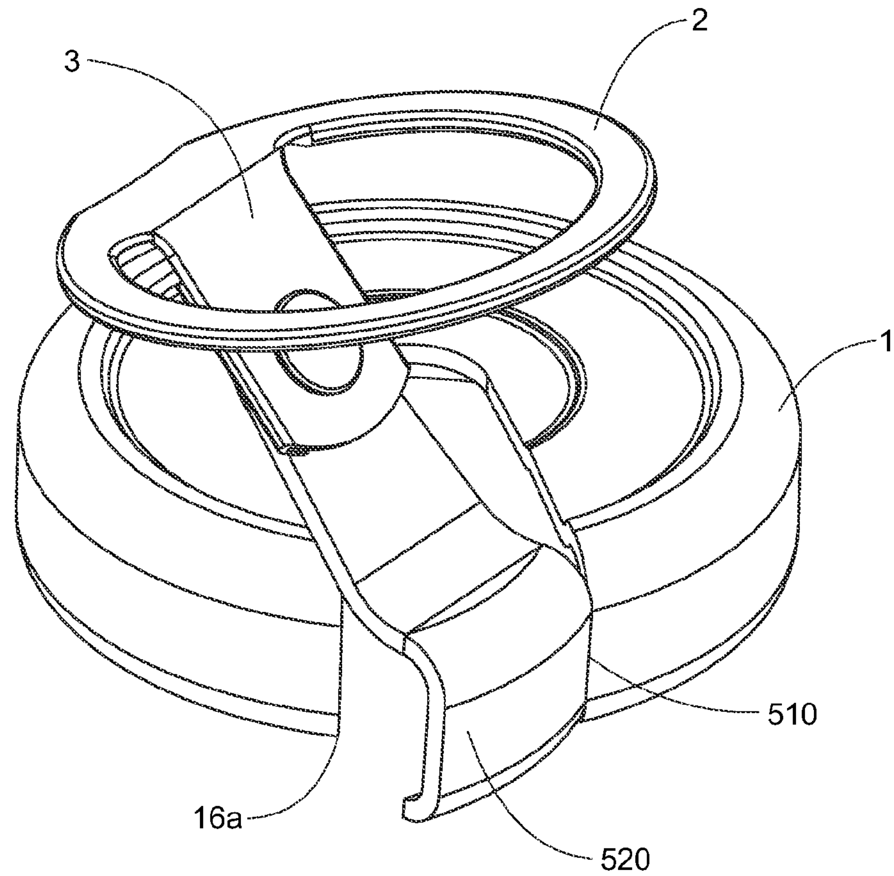
FIG. 5 is an isometric top view diagrammatic illustration of an alternative embodiment of the cap of FIG. 4, opened.

FIG. 5 is an isometric top view diagrammatic illustration of an alternative embodiment of the cap of FIG. 4, opened. Further along in the opening sequence begun in FIG. 4, frangible cap 1 is cracked open at score line 6*d* but portion 520 remains pivotally attached to crown 1 at joint 510. In the embodiment of FIG. 5, terminus 16*a* forms a substantially right angle point.

Figure 6:
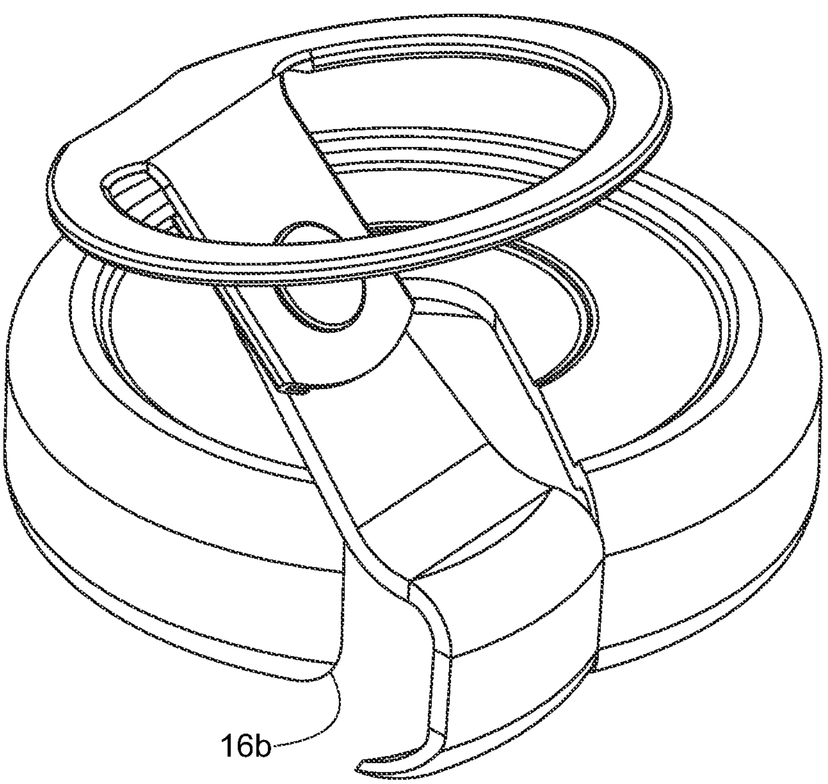
FIG. 6 is an isometric top view diagrammatic illustration of another alternative embodiment of the cap of FIG. 4, opened.

FIG. 6 is an isometric top view diagrammatic illustration of another alternative embodiment of the cap of FIG. 4, opened. At the same point in the opening sequence as FIG. 5, the alternative embodiment of FIG. 6 provides terminus 16*b* which is curved to reduce sharps.

Figure 7:
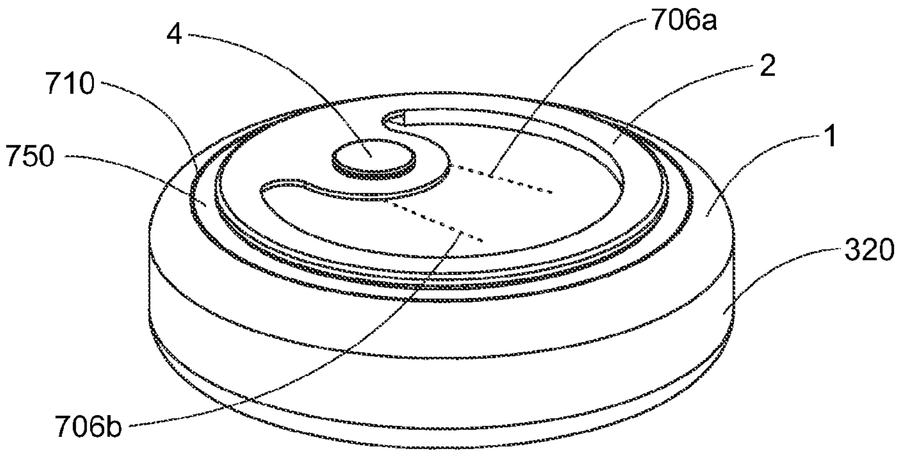
FIG. 7 is an isometric top view diagrammatic illustration of another alternative embodiment of the cap of FIG. 3.

FIG. 7 is an isometric top view diagrammatic illustration of another alternative embodiment of the cap of FIG. 3. The opener assembly is attached to cap 1 with rivet 4 and is positioned off-center. Score lines 706*a*, 706*b* do not extend from the attachment position to side 320, but instead terminate before reaching pull tab ring 2. Seam 710 circumscribes the circumference of cap 1 around the opener assembly to form cover 750.

Figure 8:
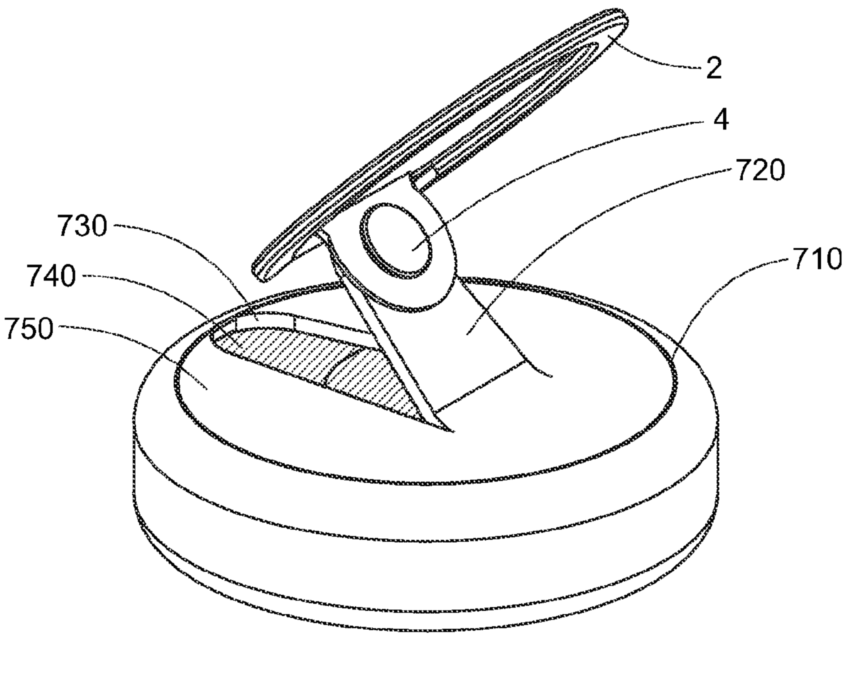
FIG. 8 is an isometric top view diagrammatic illustration of the alternative embodiment of the cap of FIG. 7, partially opened.

FIG. 8 is an isometric top view diagrammatic illustration of the alternative embodiment of the cap of FIG. 7, partially opened. The opener assembly lifts away from cap 1 by means of tab portion 720 creating opening 730. Cover 750 protects membrane 740, which is exposed upon opening.

Figure 9:
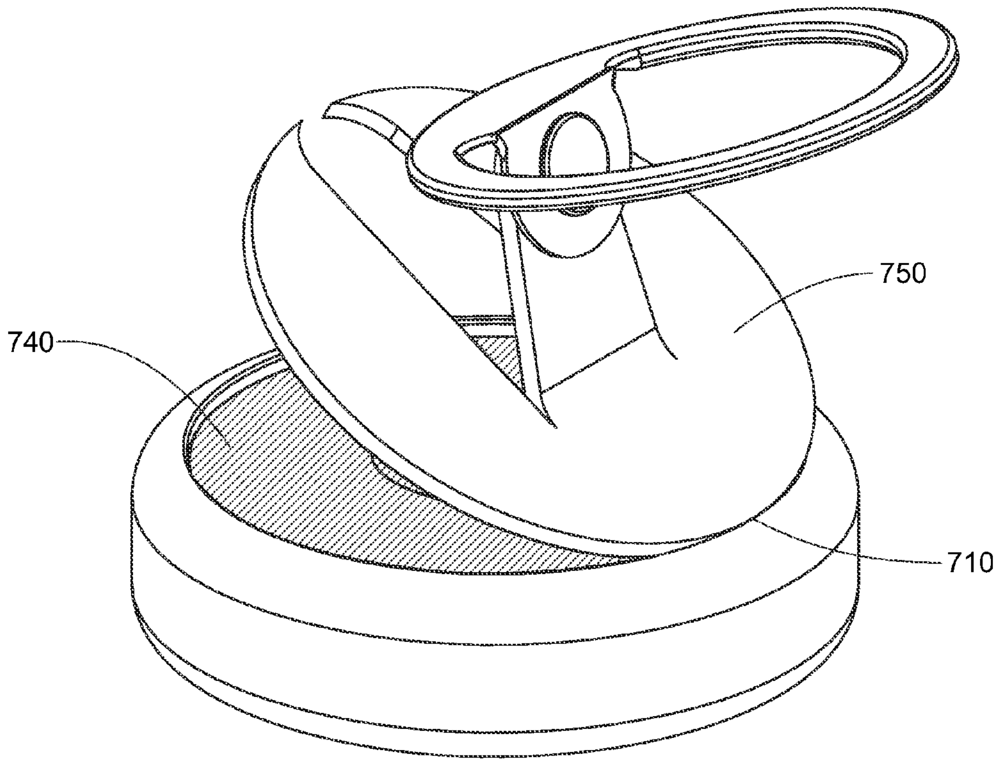
FIG. 9 is an isometric top view diagrammatic illustration of the alternative embodiment of the cap of FIG. 8.

FIG. 9 is an isometric top view diagrammatic illustration of the alternative embodiment of the cap of FIG. 8. Further along in the opening sequence of FIG. 8, more of membrane 740 is exposed and cover 750 remains pivotally attached to cap 1.

Figure 10:
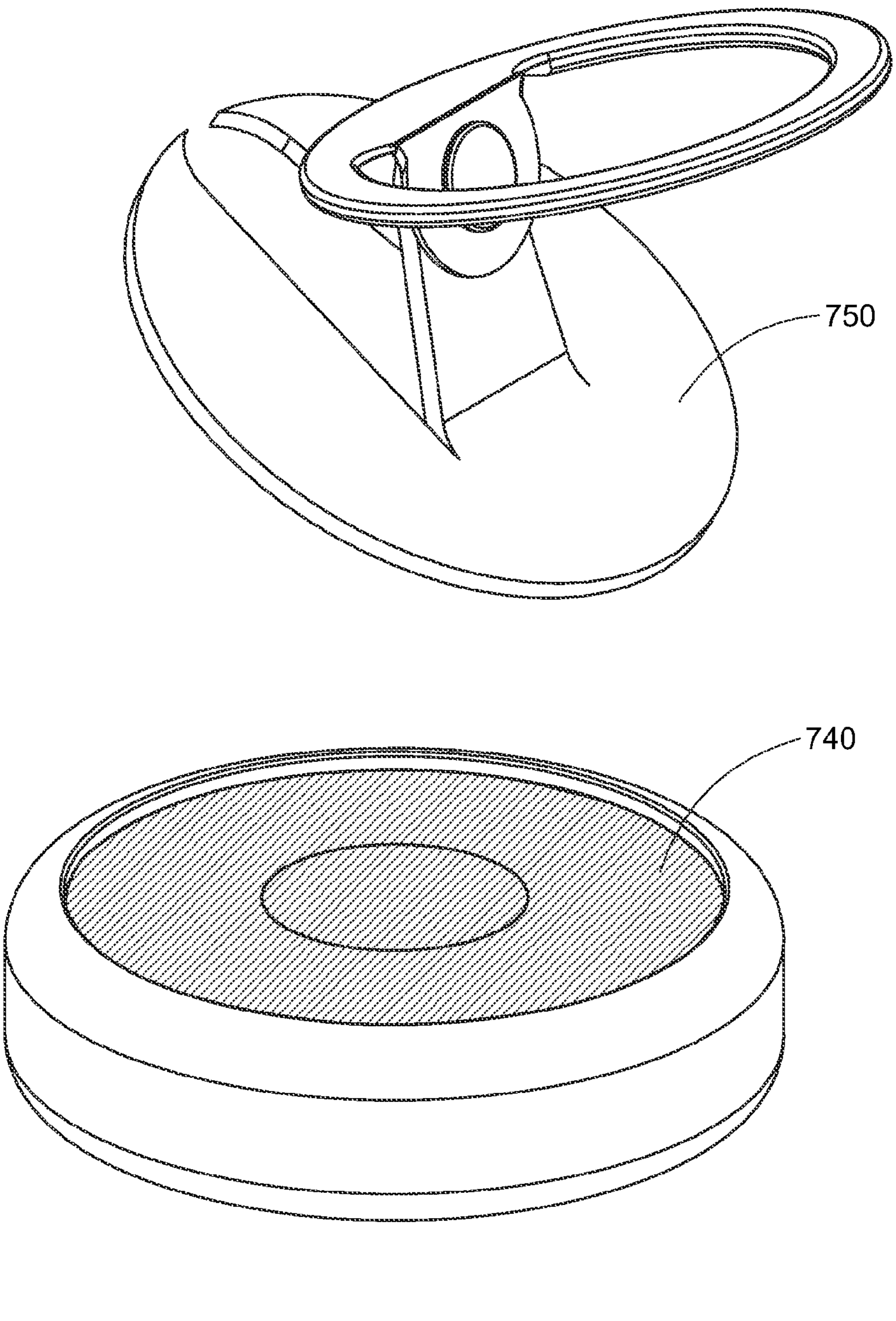
FIG. 10 is an isometric top view diagrammatic illustration of the alternative embodiment of the cap of FIG. 8 with the cover off.

FIG. 10 is an isometric top view diagrammatic illustration of the alternative embodiment of the cap of FIG. 8 with the cover off. Cover 750 is completely removed from cap 1, fully exposing membrane 740 for access by a syringe, for example.

Figure 11:
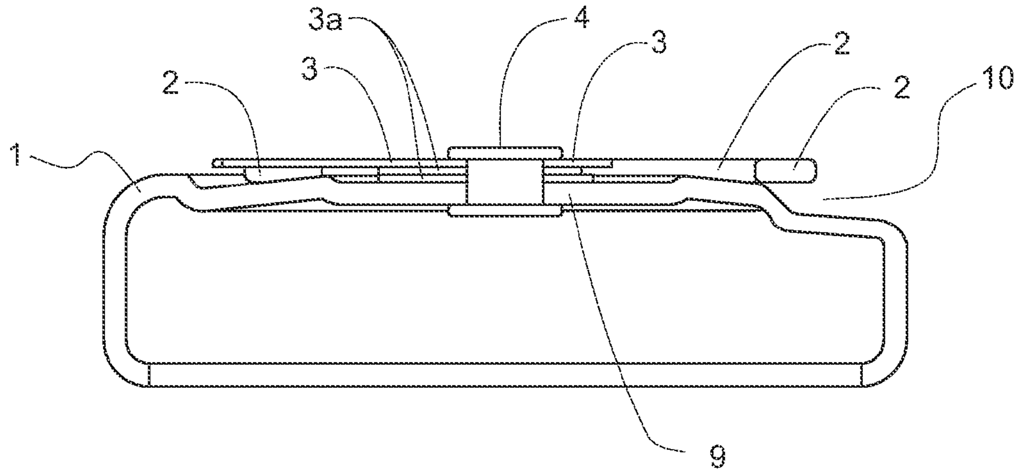
FIG. 11 is a side cross-sectional view diagrammatic illustration of an alternative embodiment of the cap of FIG. 3.

FIG. 11 is a side cross-sectional view diagrammatic illustration of an alternative embodiment of the cap of FIG. 3. Divot 10 provides a fingernail access recess to facilitate grasping pull tab ring 2.

Figure 12:
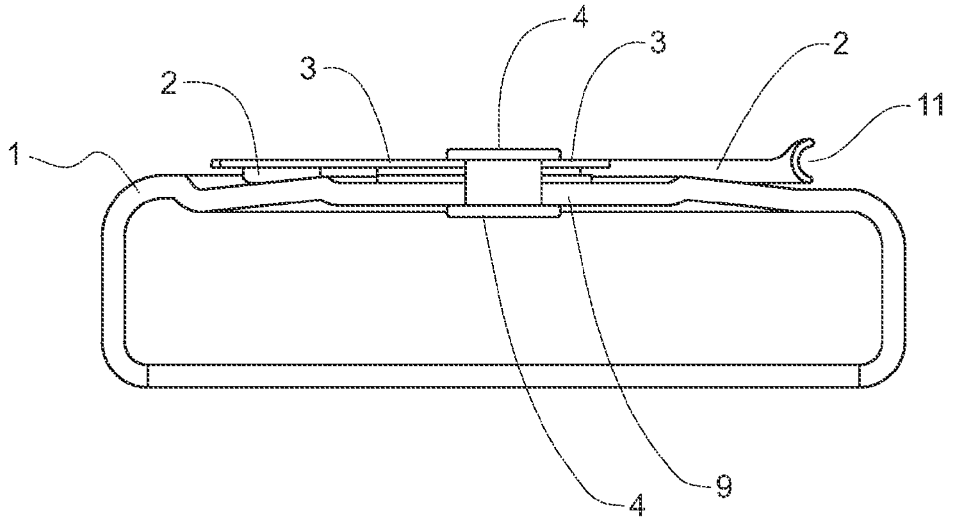
FIG. 12 is a side cross-sectional view diagrammatic illustration of another alternative embodiment of the cap of FIG. 3.

FIG. 12 is a side cross-sectional view diagrammatic illustration of another alternative embodiment of the cap of FIG. 3. In an alternative embodiment to facilitate grasping pull tab ring 2, ring 2 is provide with fingernail recess 11.

Figure 13:
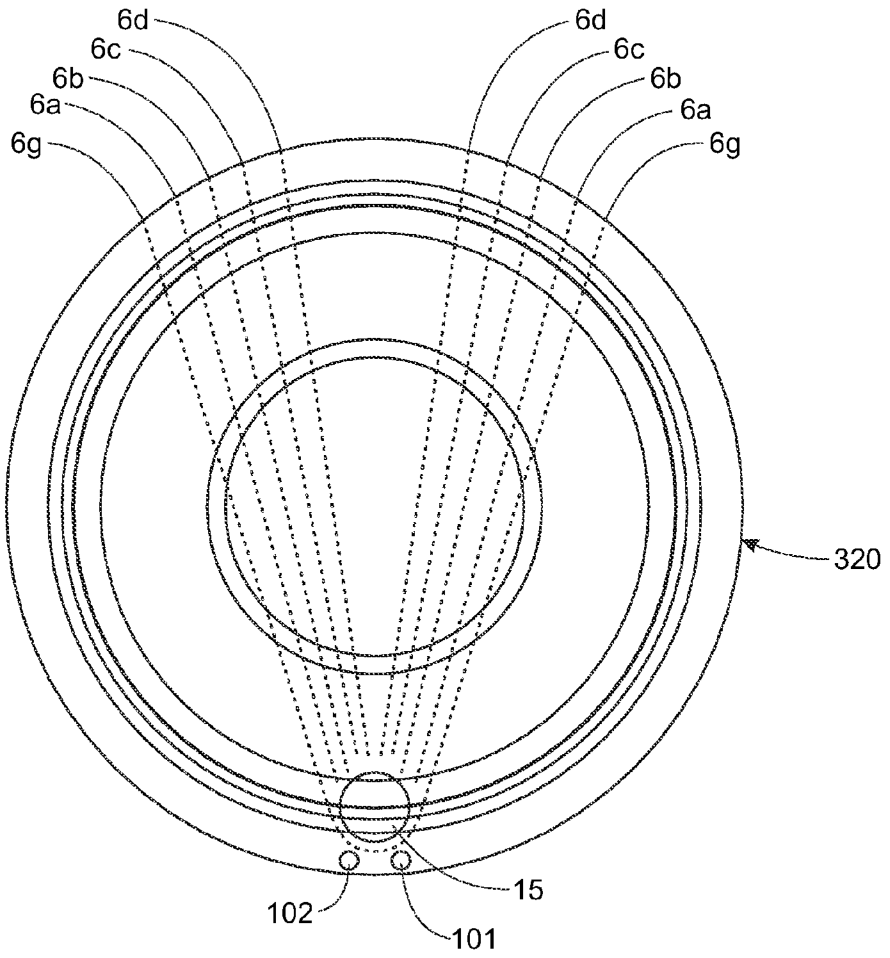
FIG. 13 is a top view diagrammatic illustration of an alternative embodiment of a medical vial cap of the present disclosure depicting alternative optional score lines and an off center attachment position for an opener assembly.

FIG. 13 is a top view diagrammatic illustration of an alternative embodiment of a medical vial cap of the present disclosure depicting alternative optional score lines and an off center attachment position for an opener assembly. Opener assembly attachment position 15 is off-center, almost to side 320. A variety of optional score line arrangements are represented by dashed lines 6*g*, 6*a*, 6*b*, 6*c*, and 6*d*. From 6*d* to 6*g*, the scores lines diverge at a wider angle. Dimples 101, 102 serve the same purpose as described above for FIG. 1. Score line 6*g* traverses around opener assembly attachment position 15, between position 15 and dimples 101, 102.

Figure 14:
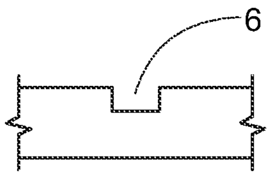
FIG. 14 is a side cross-sectional view diagrammatic illustration of a score line profile for a medical vial cap of the present disclosure.

FIG. 14 is a side cross-sectional view diagrammatic illustration of a score line profile for an alternative exemplary embodiment of a medical vial cap of the present disclosure. The score line cross-sectional profile in FIG. 14 has a substantially square or rectangular shape.

Figure 15:
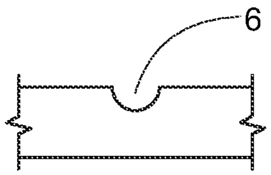
FIG. 15 is a side cross-sectional view diagrammatic illustration of an alternative score line profile for a medical vial cap of the present disclosure.

FIG. 15 is a side cross-sectional view diagrammatic illustration of an alternative score line profile for a medical vial cap of the present disclosure. The score line cross-sectional profile in FIG. 14 has a substantially arcuate or curved shape.

Figure 16:
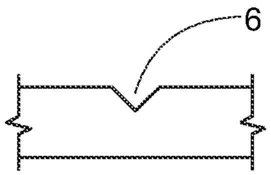
FIG. 16 is a side cross-sectional view diagrammatic illustration of another alternative score line profile for a medical vial cap of the present disclosure.

FIG. 16 is a side cross-sectional view diagrammatic illustration of another alternative score line profile for a medical vial cap of the present disclosure. The score line cross-sectional profile in FIG. 14 has a substantially v-shaped shape.

The reason score line 6 of FIGS. 24A and 24B is advantageous is that is reduces the sharps produced by tearing open crown 1 with the opener assembly. Round tear edges 6M and 6N render the opened crown dramatically less dangerous from sharps than would otherwise be the case.

Further regarding score line 6, one consideration of a crown of the present disclosure is the ease with which the material of crown 1 can be torn once opened by the opener assembly. The ease of tearing relates to the amount of pull force that needs to be applied to tear the crown material. Pulling force may be reduced, that is, ease of tearing may be increased, with the use of crown coatings or lacquers known in the art that contain additives which increase the ease of tearing, by reducing the required pull force, of the crown 1 material along line 6.

Figure 17:
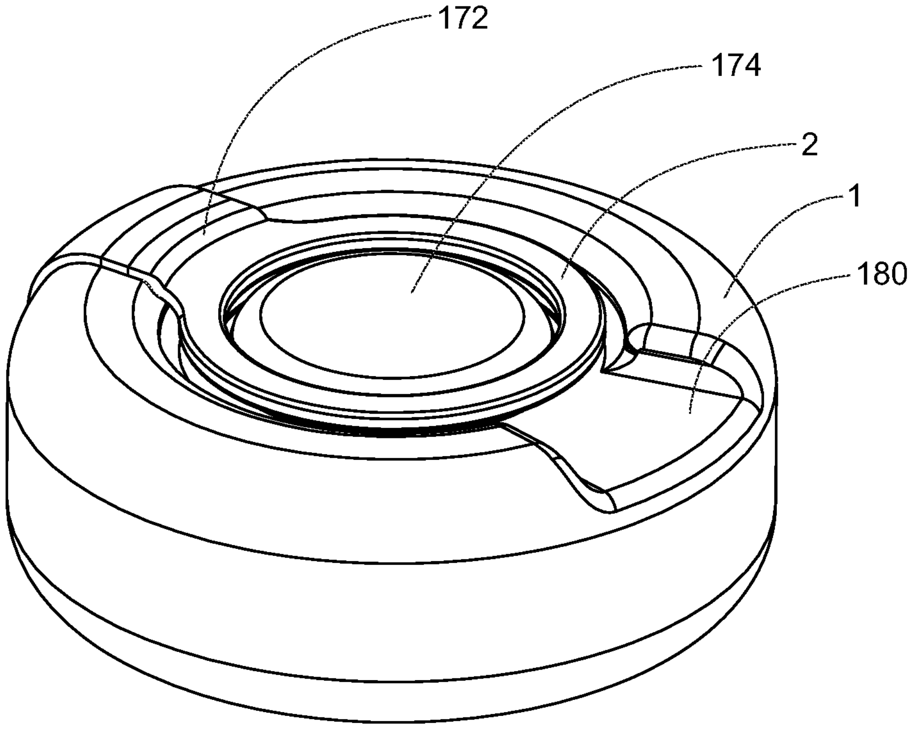
FIG. 17 is an isometric top view of an alternative embodiment of an unopened medical vial cap of the present disclosure.
Figure 18:
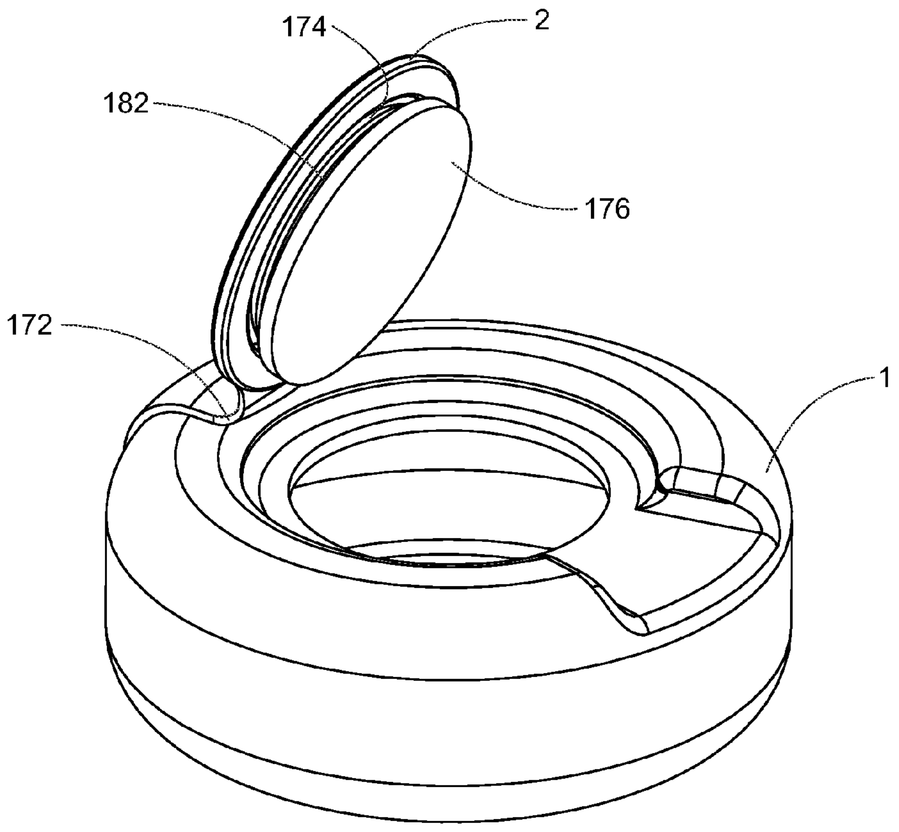
FIG. 18 is an isometric top view of an opened medical vial cap of FIG. 17.

FIG. 17 is an isometric top view of an alternative embodiment of an unopened medical vial cap of the present disclosure. FIG. 18 is an isometric top view of an opened medical vial cap of FIG. 17. FIGS. 17 and 18 will be described together. Cap 1 provides pull tab ring 2, as described above for other embodiments. However, in the embodiment of FIG. 17, pull tab ring 2 is attached to flap hinge 172 and to plug 174, which has a top portion, shown in FIG. 17, and a bottom portion 176, shown in FIG. 18. The top portion of plug 174 and bottom portion 176 form an annular receiving groove 182. Pull tab ring 2 fits snugly into groove 182 so that when pull tab ring 2 is pulled upward, plug 174 is released from the top of cap 1, pivoting on flap hinge 172, to open the cap. Pull tab ring 2, plug 174 and flap hinge 172 form an opener assembly for cap 1.

To facilitate operation of pull tab ring 2, a portion 180 of cap 1 is recessed or depressed to accommodate a human finger nail. Portion 180 makes it easier to access pull tab ring 2 with a fingernail to operate the opener assembly.

Alternative embodiments of the opener assembly of FIGS. 17 and 18 provide a plug 174 that is integral with pull tab ring 2.

Although not designed exclusively for such applications, the present vial cap is particularly useful for single use vials. Scored glass vials are in common usage for single uses but they have an inherent risk of shattering and causing lacerations. The present cap reduces such risks substantially.

A pulling force for a pull ring of the present disclosure of approximately 2.5 kg (kilograms) or less is preferred. A relatively small pull force such as this is recommended so that virtually everyone will have sufficient strength to open a bottle using a crown of the present disclosure. In contrast, a relatively large pull force has the disadvantage of requiring a great amount of initial force to tear the tinplate material, and once the cap material is torn open the sudden release of pulling force causes the bottle to jerk away from the user, spilling the contents often in dramatic fashion.

In addition to the low hardness of the crown material, the thinness or gauge of the crown may also contribute to achieving a small pull force. For example, a crown of the present invention is recommended to have a thickness of less than 0.28 mm Embodiments in which the crown material is strengthened by corrugation, such as in seated embodiments of FIGS. 3, 17, and 18, may be thinner than standard crowns, having, for example, a gauge as thin as approximately 0.16 mm.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural, materials, and logical substitutions and changes may be made without departing from the scope of this disclosure. Figures are merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the claims reflect, inventive subject matter lies in less than all features of a single disclosed embodiment. Thus the following claims are hereby incorporated into the Detailed Description, with each claim standing on its own as a separate embodiment.

The description has made reference to several exemplary embodiments. It is understood, however, that the words that have been used are words of description and illustration, rather than words of limitation. Changes may be made within the purview of the appended claims, as presently stated and as amended, without departing from the scope and spirit of the disclosure in all its aspects. Although description makes reference to particular means, materials and embodiments, the disclosure is not intended to be limited to the particulars disclosed; rather, the disclosure extends to all functionally equivalent technologies, structures, methods and uses such as are within the scope of the appended claims.

I claim:

1. A crown for a medical vial opening, the crown comprising:

a top portion disposed over a pierceable membrane substantially coextensive with the top portion;

a skirt surrounding the top portion and terminating at a lower edge defined in a first horizontal plane;

an opener assembly mounted to a part of the top portion;

a first scoring line extending from the portion of the top to which the opener assembly is mounted towards the skirt in a continuous radial direction;

a second scoring line extending from the part of the top portion to which the opener assembly is mounted towards the skirt along a radial axis; and. wherein the opener assembly is operable to remove the top portion from the skirt thereby exposing the pierceable membrane.

2. The crown of claim 1, wherein the opener assembly further comprises a pull tab having a tab portion secured to the part of the top portion of the crown and a pull tab ring extending from the tab portion.

3. The crown of claim 2, further comprising a rivet securing the pull tab to the top portion of the crown.

4. The crown of claim 2, wherein the pull tab ring comprises a recess formed on an edge thereof configured for fingernail access by a user of the opener assembly.

5. The crown of claim 1, wherein the top portion comprises a divot between the pull tab ring and the top portion configured for fingernail access by a user of the opener assembly.

6. The crown of claim 2, wherein a connection between the tab portion and the pull ring is deformable such that the pull ring may be lifted from the top portion of the crown.

7. The crown of claim 1, wherein the part of the top portion to which the opener assembly is mounted is radially off-set with respect to a center of the top portion.

8. The crown of claim 1, wherein at least one of the first or second score lines comprises a curve-shaped cross-section.

9. The crown of claim 1, wherein a circumference of the skirt surrounding the top portion comprises a recessed depression sufficient to house the opener assembly substantially flush with a top height of the crown.

10. The crown of claim 1, wherein the first and second scoring lines are non-parallel.

* * * * *